(12) United States Patent
Enggaard et al.

(10) Patent No.: US 8,920,383 B2
(45) Date of Patent: *Dec. 30, 2014

(54) DOSE MECHANISM FOR AN INJECTION DEVICE FOR LIMITING A DOSE SETTING CORRESPONDING TO THE AMOUNT OF MEDICAMENT LEFT

(75) Inventors: Christian Peter Enggaard, Hillerod (DK); Claus Schmidt Moller, Fredensborg (DK); Tom Hede Markussen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/996,409

(22) PCT Filed: Jul. 17, 2006

(86) PCT No.: PCT/EP2006/007004
§ 371 (c)(1),
(2), (4) Date: Jun. 2, 2008

(87) PCT Pub. No.: WO2007/017052
PCT Pub. Date: Feb. 15, 2007

(65) Prior Publication Data
US 2008/0243087 A1    Oct. 2, 2008

Related U.S. Application Data

(60) Provisional application No. 60/708,618, filed on Aug. 16, 2005.

(30) Foreign Application Priority Data

Jul. 27, 2005   (EP) ..................................... 05016291

(51) Int. Cl.
*A61M 5/00* (2006.01)
*A61M 5/315* (2006.01)
*A61M 5/20* (2006.01)

(52) U.S. Cl.
CPC ....... *A61M 5/31583* (2013.01); *A61M 5/31571* (2013.01); *A61M 5/31586* (2013.01); *A61M 5/31553* (2013.01); *A61M 2005/202* (2013.01); *A61M 5/20* (2013.01); *A61M 5/31593* (2013.01); *A61M 5/31541* (2013.01); *A61M 5/3156* (2013.01)
USPC ........................................................ 604/207

(58) Field of Classification Search
USPC .................. 604/181, 187, 207–211, 218–231
See application file for complete search history.

(56) References Cited

U.S. PATENT DOCUMENTS

| 4,865,591 A | 9/1989 | Sams |
| 5,104,380 A | 4/1992 | Holman et al. |

(Continued)

FOREIGN PATENT DOCUMENTS

| DE | 20209051 U1 | 4/2003 |
| DE | 69810860 | 11/2003 |

(Continued)

OTHER PUBLICATIONS

Non-Final Office Action issued by the PTO for U.S. Appl. No. 11/996,397 dated Dec. 31, 2008.

(Continued)

*Primary Examiner* — Kevin C Sirmons
*Assistant Examiner* — Deanna K Hall
(74) *Attorney, Agent, or Firm* — Wesley A. Nicolas; Reza Green; Richard W. Bork (57) ABSTRACT

A mechanism for preventing setting of a dose, which exceeds the amount of a medicament in a reservoir in an injection device. The device comprises a threaded piston rod, a limiter and a driver. The three elements are arranged such that during dose setting, the limiter is moved towards an end-of-contend position, wherein dose setting is limited. The invention comprises an accumulative and a non-accumulative embodiment. The invention further relates to a mechanism for prevention ejection of a dose exceeding the set dose.

13 Claims, 7 Drawing Sheets

(56) References Cited

U.S. PATENT DOCUMENTS

| | | | |
|---|---|---|---|
| 5,938,642 A * | 8/1999 | Burroughs et al. | 604/208 |
| 6,221,046 B1 | 4/2001 | Burroughs et al. | |
| 6,569,123 B2 | 5/2003 | Alchas et al. | |
| 6,582,404 B1 * | 6/2003 | Klitgaard et al. | 604/181 |
| 6,585,698 B1 | 7/2003 | Packman et al. | |
| 6,663,602 B2 | 12/2003 | Moller | |
| 2002/0120235 A1 * | 8/2002 | Enggaard | 604/135 |
| 2002/0165500 A1 | 11/2002 | Bechtold et al. | |
| 2005/0033244 A1 | 2/2005 | Veasey et al. | |

FOREIGN PATENT DOCUMENTS

| | | |
|---|---|---|
| DE | 10229122 A1 | 2/2004 |
| DE | 10351596 A1 | 6/2005 |
| EP | 0897728 | 2/1999 |
| EP | 0937471 | 8/1999 |
| EP | 937476 A2 | 8/1999 |
| EP | 5016291.6 | 7/2005 |
| EP | 1909870 A1 | 4/2008 |
| JP | 2002-503116 A | 1/2002 |
| JP | 2005-508205 A | 3/2005 |
| RU | 2091087 C1 | 9/1997 |
| RU | 2212254 C2 | 9/2003 |
| SU | 1528330 A3 | 12/1989 |
| WO | 8702895 A1 | 5/1987 |
| WO | WO 87/02895 | 5/1987 |
| WO | 96/27400 A1 | 9/1996 |
| WO | 9938554 | 8/1999 |
| WO | 01/19434 A1 | 3/2001 |
| WO | 0195959 A1 | 12/2001 |
| WO | 02/053214 | 7/2002 |
| WO | 02/092153 A2 | 11/2002 |
| WO | 03/011374 A1 | 2/2003 |
| WO | 2004/007003 A1 | 1/2004 |
| WO | 2004/028598 A1 | 4/2004 |
| WO | 2004/030730 A2 | 4/2004 |
| WO | 2004/078240 A2 | 9/2004 |
| WO | 2005018721 | 3/2005 |
| WO | 2006045526 A1 | 5/2006 |
| WO | 2006/058883 | 6/2006 |
| WO | 2006076921 | 7/2006 |
| WO | 2006/089768 A1 | 8/2006 |
| WO | 2006/114395 A1 | 11/2006 |
| WO | 2006/125328 A1 | 11/2006 |
| WO | 2006/125329 A1 | 11/2006 |

OTHER PUBLICATIONS

Non-Final Office Action issued by the PTO for U.S. Appl. No. 11/996,397 dated Aug. 25, 2009.
Final Rejection in U.S. Appl. No. 11/996,397, filed Jan. 1, 2008 by Eiland et al. Mailed Apr. 20, 2010.
Statement by Dr. Nils Basso printed May 8, 2010.
Description of the Mechanical Components of the OPTICLIK Pen printed May 8, 2010.
YPSOMED AG Press Release Jan. 16, 2005 (German and English versions).
Notice of Opposition in EP1909870 dated Dec. 12, 2011.
Google translations of Depositions in Opposition of EP 1909870 dated Dec. 12, 2011.

* cited by examiner

DOSE MECHANISM FOR AN INJECTION DEVICE FOR LIMITING A DOSE SETTING CORRESPONDING TO THE AMOUNT OF MEDICAMENT LEFT

CROSS-REFERENCE TO RELATED APPLICATIONS

This application is a 35 U.S.C. §371 national stage application of International Patent Application PCT/EP2006/007004 (published as WO 2007/017052), filed Jul. 17, 2006, which claimed priority of European Patent Application 05016291.6, filed Jul. 27, 2005; this application further claims priority under 35 U.S.C. §119 of U.S. Provisional Application 60/708,618, filed Aug. 16, 2005.

FIELD OF THE INVENTION

The present invention relates to a mechanism for preventing setting of a dose which exceeds the amount of a medicament in a reservoir in an injection device. In particular, the present invention relates to a mechanism wherein the piston rod forms part of said mechanism, whereby a compact structure may be provided.

BACKGROUND OF THE INVENTION

When drugs are to be injected into the human body, it is essential that the dose set by the user is the actual dose injected. If this is not the case, the medicating of the patient is not correct, which in some cases can have serious or even fatal consequences. In order to ensure that the dose selected by a dose setting member does not exceed the remaining amount of medication in a reservoir in a syringe device, an end-of-content mechanism may be provided.

End-of-content mechanisms are known in the art. One such example may be seen in WO 01/19434 A1 which discloses a limiting mechanism for an injection device. A dose is injected by rotating a dose setting member which during this rotation carries a driver with it to rotate this driver which moves a piston forward. The driver is provided with a track having a length which is engaged by a track follower coupled to the dose setting mechanism.

Another example may be seen in WO 2004/007003 A1.

It is an object of a preferred embodiment of the present invention to provide an alternative to the above solution. Especially, it is an object of the present invention to provide a solution which allows an outer surface of a driver to be directly coupled to the inner surface of a drum scale, and thus it is an object of the present invention to provide an end-of-content mechanism which may be positioned in the space defined by the inner walls of a driver.

SUMMARY OF THE INVENTION

The present invention provides an accumulative and a non-accumulative solution to the above problems.

In the accumulative solution which is described below under a first general embodiment of the invention a limiter is moved stepwise closer to a stopping position wherein the limiter acts together with other elements of the preventing mechanism to ensure that it is not possible to set a dose exceeding the amount of medicament left in a reservoir.

In the non-accumulative solution which is described under the second general embodiment of the invention the limiter is positioned in the same position prior to dose setting and after dose ejection.

The present invention relates to a mechanism for preventing setting of a dose which exceeds the amount of a medicament in a reservoir in an injection device, wherein a dose is set by rotating a dose setting member of a dose setting mechanism, the mechanism comprising:
 a piston rod having a threaded outer surface;
 a limiter defining a passage for the piston rod;
 a driver defining a passage for the limiter, the driver being coupled to the dose setting member such that rotation of the dose setting member during dose setting causes the driver to rotate; and
wherein the limiter is coupled to the driver and the piston rod such that relative rotation between the driver and the piston rod during dose setting causes the limiter to move towards a stopping position wherein the limiter prevents setting of a dose which exceeds the amount of a medicament in a reservoir in the injection device.

The mechanism may further comprise a housing defining a passage for the piston rod, the passage may have a threaded inner surface for engagement with the threaded outer surface of the piston rod, the housing may be arranged with respect to the piston rod such that rotation of the piston rod, in relation to the housing, causes the piston rod to be displaced relative to the housing in a longitudinal direction. The housing may form part of the housing of a syringe device into which the mechanism is integrated.

The mechanism may comprise a locking means for locking the piston rod against rotation in at least one direction, relative to the housing. Such a locking means may be a screw which may engage or disengage the piston rod. Advantageously, the screw may be arranged such that it engages a root part of the piston rod, whereby the walls of the thread and especially not the crest are not damaged. Alternatively, the locking means may be provided as a pivotable arm, which is operable from an outer surface of the device. The pivotable arm may be movable between an engaging and a non-engaging position, by means of an arm or button accessible from the outer surface of the syringe device.

The mechanism may comprise a ratchet mechanism interconnecting the driver and the housing. The ratchet mechanism may comprise a first and a second part. The first part may be coupled to the driver while the second part may be coupled to the housing e.g. via the locking means. The ratchet mechanism may be adapted to move in one or two rotational directions.

In order to assist patients with poor dexterity an ejection assisting system for providing an ejection force for assisting an operator during ejection may be provided. Such a system may comprise a spring which is strained when the dose setting member is rotated during dose setting. The spring may interconnect the housing and the first part of the ratchet e.g. in such a way that it co-extend the piston rod. Accordingly, when the driver is rotated by means of the dose setting member, whereby the first part of the ratchet is rotated, the spring is rotationally strained. The potential energy stored in the strained spring is released by disengaging the locking means whereby the ratchet mechanism is free to move, whereby the strained spring forces the ratchet mechanism to rotate. As the second part of the ratchet mechanism may be locked for rotation in relation to the piston rod, the rotating ratchet mechanism carries the piston rod with it.

In one embodiment the spring is pre-strained, such as one revolution, such as two revolutions, such as three revolutions, such as four revolutions, such as five revolutions.

In the context of the present invention the term "stopping thread" shall be understood as engaging threads of two elements, at least one of which threads prevents a first of the two elements from being rotated beyond a predetermined position relative to a second of the two elements. Normally, said prevention of rotation is caused by engagement of surfaces of each of the two elements.

In the following a first general embodiment of the invention is described.

In a FIRST general embodiment the present invention relates to a mechanism for preventing setting of a dose which exceeds the amount of a medicament in a reservoir in an injection device, wherein a dose is set by rotating a dose setting member of a dose setting mechanism, the mechanism comprising:

- a piston rod having a threaded outer surface;
- a limiter defining a passage for the piston rod and being rotationally retained in relation to the piston rod, the limiter having a threaded outer surface;
- a driver defining a passage for the limiter, the passage having a threaded inner surface for engagement with the threaded outer surface of the limiter, the driver being coupled to the dose setting member such that rotation of the dose setting member during dose setting causes the driver to rotate; and wherein relative rotation between the driver and the piston rod during dose setting causes the limiter to move towards a stopping position wherein the limiter prevents setting of a dose which exceeds the amount of a medicament in a reservoir in the injection device.

Rotation of the dose setting member during dose setting causes the driver to rotate. If the direction of rotation of the dose setting member and the driver is the same, the driver and the dose setting member may be made as one single unit. Alternatively, the two elements may be made be two separate elements attached or coupled to each other.

The direction of the thread of the piston rod and the driver may be opposite i.e. if the piston rod has a right-handed thread, the driver has a left-handed thread and vice versa. This ensures that the dose setting member is rotated back to the same position such that the user may set a dose starting from an initial dose of 0 IU.

The limiter may comprise a first engaging surface adapted to engage a corresponding second engaging surface of the driver. In one embodiment the limiter comprises a plurality of first engaging surfaces which are adapted to engage corresponding second engaging surfaces of the driver. In some embodiments, the number of first and second engaging surfaces is not identical. As an example there may be provided two first engaging surfaces while there is provided ten second engaging surfaces. Accordingly, the limiter may be locked in relation to each other in ten different positions, but at each position only two first and two second engaging surfaces engage each other.

The threaded outer surface of the piston rod may comprise the first surface and the threaded inner surface of the driver comprises the second surface. The piston rod and the driver may be arranged such that relative rotational movement may cause the first and the second surface to be brought into engagement, whereby further relative rotational movement is not possible.

Alternatively, the limiter may comprise a plurality of teeth adapted to engage corresponding teeth of the housing and/or the driver when the limiter is in the stopping position.

Accordingly, the teeth of the limiter comprise first engaging surfaces, while the teeth of the housing and/or driver may comprise the second stopping surfaces.

In one embodiment there is provided both teeth and a stopping thread. An advantage of this is that a larger torque may be transferred from the driver to the limiter, whereby it may be ensured that even when applying a large torque to the dose setting mechanism, a dose which exceeding the actual amount left in the reservoir cannot be set. Such a larger torque may be between 100 and 1000 Nmm, such as 250 Nmm, such as 500 Nmm, such as 750 Nmm.

In the following a second general embodiment of the invention is described.

In a SECOND general embodiment the present invention relates to a mechanism for preventing setting of a dose which exceeds the amount of a medicament in a reservoir in an injection device, wherein a dose is set by rotating a dose setting member of a dose setting mechanism, the mechanism comprising:

- a piston rod having a threaded outer surface;
- a limiter defining a passage for the piston rod, the passage having a threaded inner surface for engagement with the threaded outer surface of the piston rod;
- a driver defining a passage for the limiter, the driver being rotationally retained in relation to the limiter, the driver being coupled to the dose setting mechanism such that rotation of the dose setting member during dose setting causes the driver to rotate; and wherein relative rotation between the driver and the piston rod during dose setting causes the limiter to move towards a stopping position wherein the limiter prevents setting of a dose which exceed the amount of a medicament in a reservoir in the injection device As described above the invention according to the second general embodiment of the invention is a non-accumulative solution, wherein the limiter is positioned in the same position (the reference position) prior to dose setting and after dose ejection. The limiter may comprise a first engaging surface adapted to engage a corresponding second engaging surface of the piston rod. The engaging surface of the limiter may be an end surface extending in a radial direction of the limiter and facing a corresponding radial surface of a T-shaped piston rod. Accordingly, when the piston rod is rotated relative to the limiter, the two surfaces will abut each other such that the user is prevented from setting a higher dose. In the alternative the threaded outer surface of the piston rod comprises the first surface and the threaded inner surface of the driver comprises the second surface. The two latter surfaces may each define a plane parallel with the axis of the piston rod and the limiter.

DESCRIPTION OF THE DRAWINGS

The invention will now be described in further detail with reference to the drawings, in which.

Figure 1:
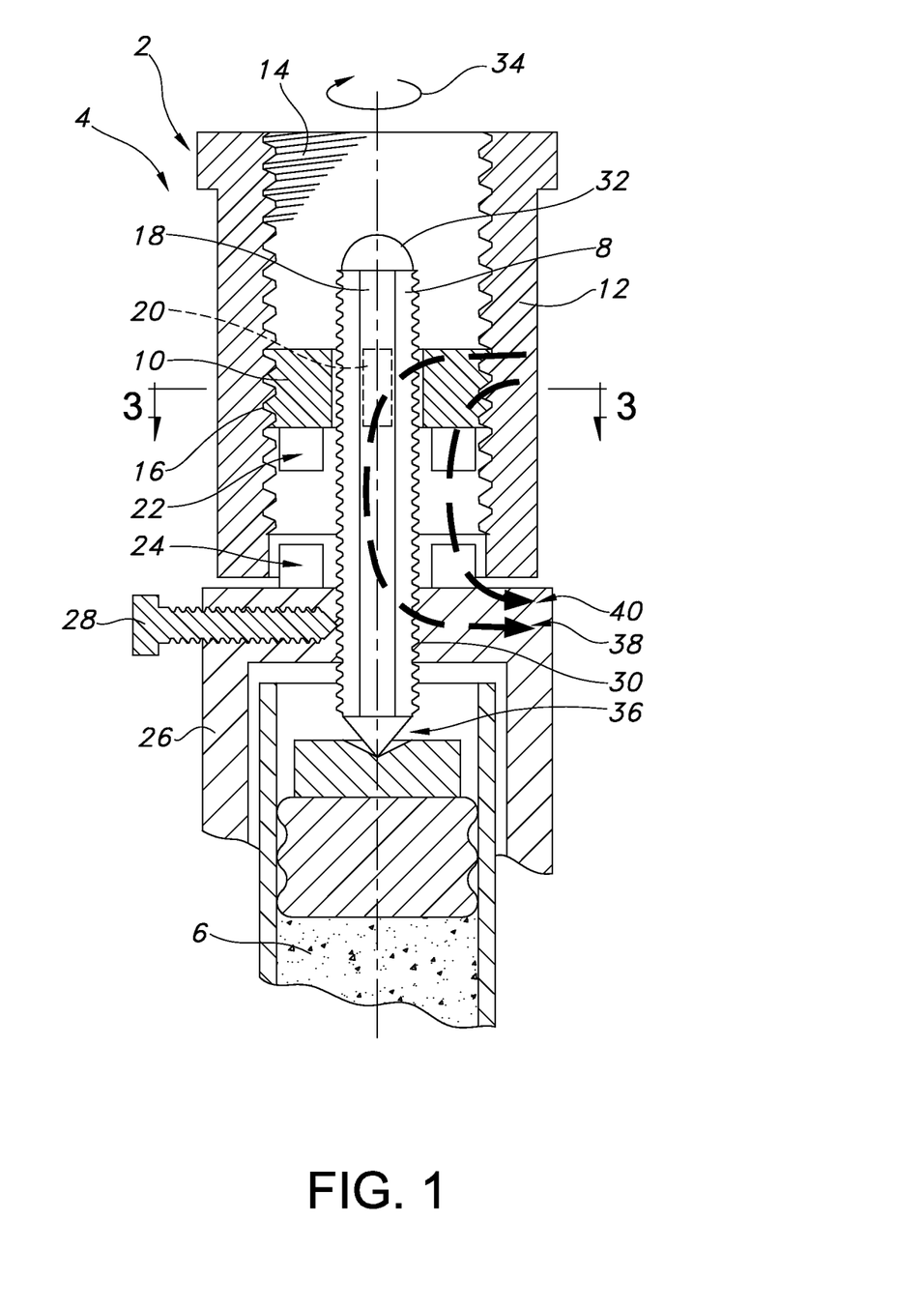
FIG. 1 illustrates a mechanism according to the first general embodiment of the invention.

FIG. 1 discloses syringe device 2 comprising a mechanism 4 for preventing setting of a dose which exceeds the amount of a medicament in a reservoir 6. The mechanism 4 comprises a piston rod 8, a limiter 10 and a driver 12. The driver is coupled to a dose setting member (not shown) such that rotation of the dose setting member during dose setting, causes the driver to rotate in the same direction—both when dialling up and down. The inner surface 14 of the driver 12 has a threaded surface which is adapted to engage a corresponding thread of the outer surface 16 of the limiter 10. Moreover, the limiter 10 is locked for rotation in relation to the piston rod 8 by means of groove 18 in the piston rod 8 and a tongue 20 in the limiter 10 (in the figure the tongue is indicated by a dotted line). Due to the grove-tongue arrangement the limiter 10 and the piston rod 8 may move translationally (i.e. up and down in the figure) in relation to each other.

The limiter comprises a first set of teeth 22 adapted to engage a second set of teeth 24 of the housing 26. The function of the teeth is to ensure that the dose set does not exceed the amount of a medicament left in the reservoir 6. Furthermore, the threads of the inner surface 14 and the outer surface 16 comprises a stopping thread which are also used to ensure that that the user cannot set a dose which exceed the amount of a medicament in the reservoir. The two systems are redundant and designed to stop dose setting simultaneously.

The syringe device further comprises a locking means 28 in the form of a screw, which is used to lock the piston rod 8 for rotation in relation to the housing 26. Due the threaded engagement 30 between the housing 26 and the piston rod 8, rotational locking of said two elements, results in a translational lock. When the locking means is in the form of a screw, it is desirable that the tip of the screw engages the piston rod in a root of the thread, such that the crest of the thread is not damaged.

In the initial state i.e. when the pen is delivered to the user, the limiter 10 is located in proximal end 32 of the piston rod (i.e. the end opposite the needle of the syringe device).

In order to set a dose the user locks the piston rod for rotation by means of the locking means 28. The dose is then set by rotating the driver as indicated by the arrow 34. Due to the relative rotational movement between the piston rod 8 and the driver 12 the limiter 10 moves towards in a distal end 36 of the piston rod.

When the desired dose has been set, the driver, the limiter and the piston rod are locked rotationally in relation to each other such that when a dose is ejected, they all rotate together. Due to the threaded engagement 30 between the housing and the piston rod 8, the rotation of the piston rod causes the piston rod to move in the distal direction. However, due to the grove-tongue between the piston rod and the limiter, the translational movement of the piston rod is not transmitted to the limiter and the driver. Accordingly, the limiter (and the driver) remains in the same longitudinal position.

It will be appreciated, that during each dose setting the limiter moves closer to the stopping position in which the first and second set of teeth engage and wherein the stopping thread engage. In this position the driver cannot be rotated further, and any torque applied to the dose setting member by the user is transferred from the dose setting member to the driver and via two torque paths. When the torque is transferred through the first torque path 38, it is transferred from the driver to the limiter, further through the grove-tongue connection to the piston rod and finally from the piston rod to the housing, due to the rotational locking means 28. When the torque is transferred through the second torque path 40 it is transferred from the driver to the limiter, further from the first set of teeth 22 to the second set of teeth 24 of the housing. By providing a first torque path and a second torque path it is possible to apply a larger torque without breaking the parts of the device e.g. the teeth, and, thus, the risk of user causing damage to the device is reduced.

Figure 2:
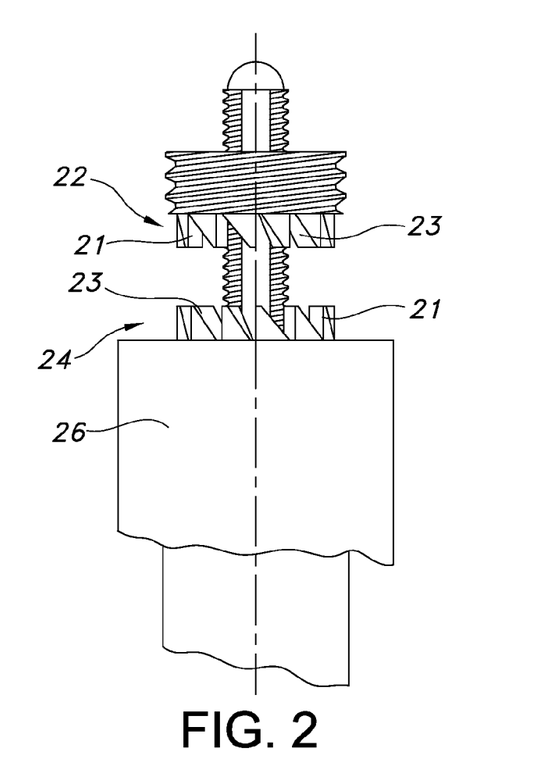
FIG. 2 illustrates teeth of the limiter and the housing according to the first general embodiment.

FIG. 2 shows the housing 26 comprising the second set of teeth 24 which are adapted to engage the first set of teeth 22 of the housing. Each tooth may have a one surface 21 which is substantially parallel with the axial direction of the limiter and another surface 23 which is transverse to said axial direction.

Figure 3:
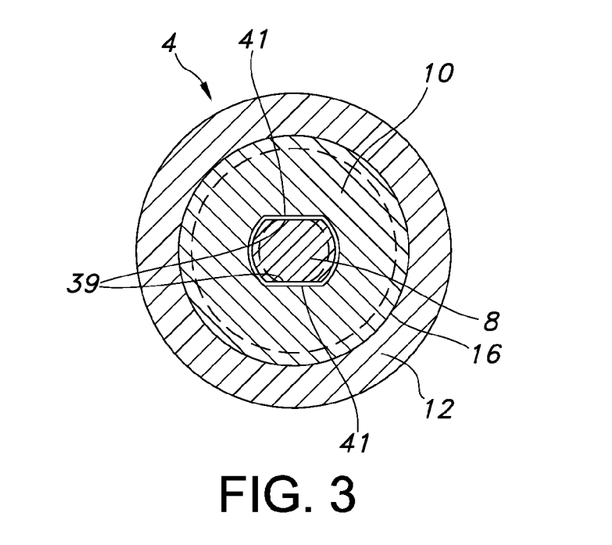
FIG. 3 illustrates a cross-section through of the piston rod, the limiter and the driver of FIG. 1.

FIG. 3 discloses an alternative to the grove-tongue described in connection with FIG. 1. In the alternative the piston rod 8 has two flat surfaces 39 and due to corresponding flat surfaces 41 of the limiter 10, the limiter and the piston rod are locked for relative rotational movement.

Figure 4:
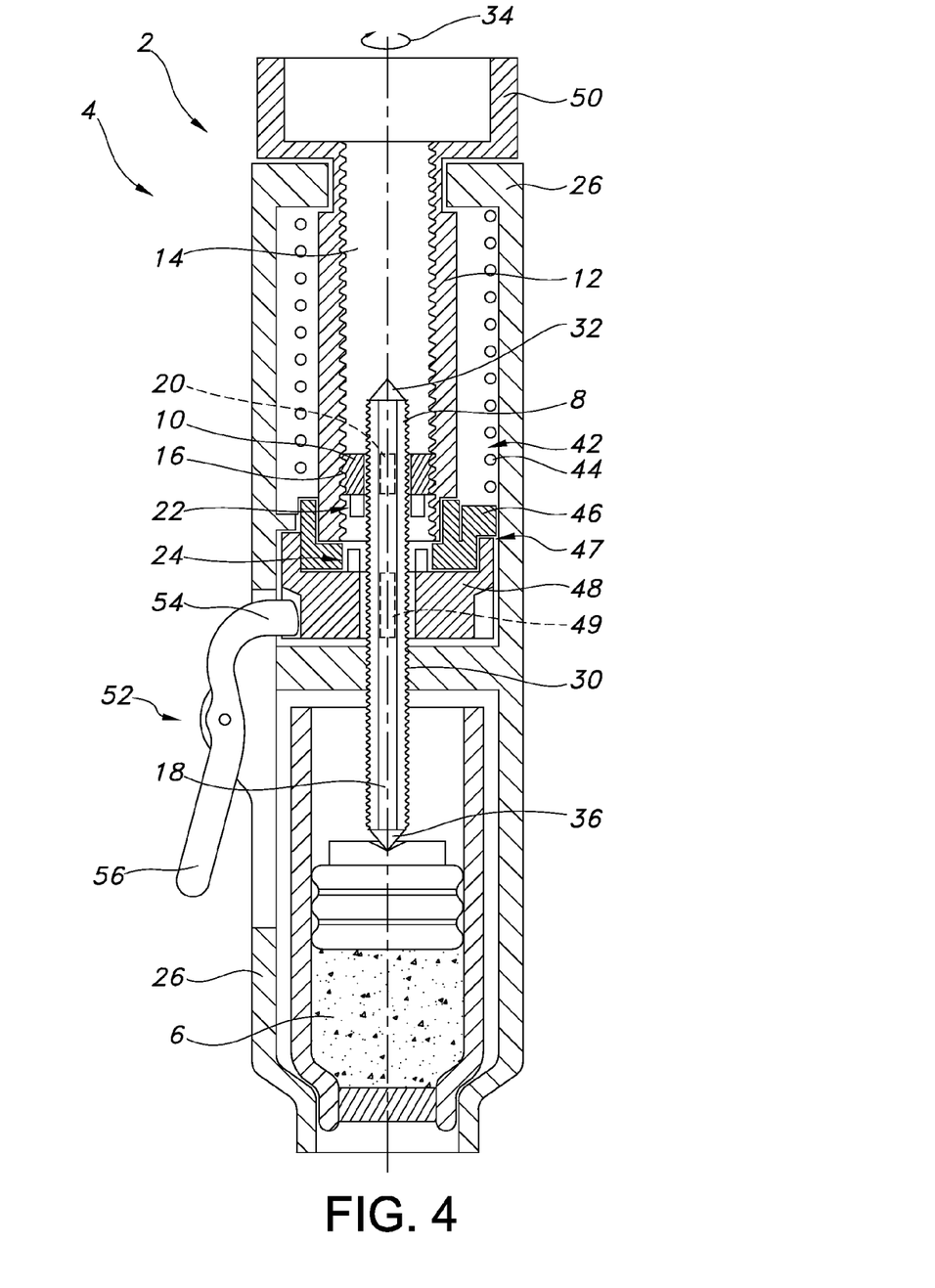
FIG. 4 illustrates a syringe device with injection assisting means and a mechanism according to the first general embodiment of the invention.

FIG. 4 discloses a syringe device 2 comprising the mechanism 4 described in relation to FIG. 1. However, the syringe device of FIG. 4 further comprises an injection assisting mechanism 42 comprising a spring 44 interconnecting the housing 26 and a first part 46 of a ratchet mechanism 47, which further comprises a second part 48. When the dose setting member 50 is rotated, the rotation is transferred to the driver 12 and the first part 46 of the ratchet mechanism. During the rotation of the dose setting member, the spring 44 is strained whereby potential energy is stored. The stored energy may be released by disengaging the pawl 52 which during dose setting engages the second part 48 of the ratchet mechanism. The pawl 52 is pivotally connected to the housing and comprises an engaging part 54 and a button part 56. When the pawl is disengaged the strained spring 44 causes the first part 46 to rotate. Due to the engagement between the first part 46 and the second part 48, and due to the grove-tongue connection 49 between the second part 48 and the piston rod 8, the rotation of the first part 46 causes the piston rod to rotate. As described under FIG. 1 the rotation of the piston rod causes the piston rod to move forward.

Figure 5:
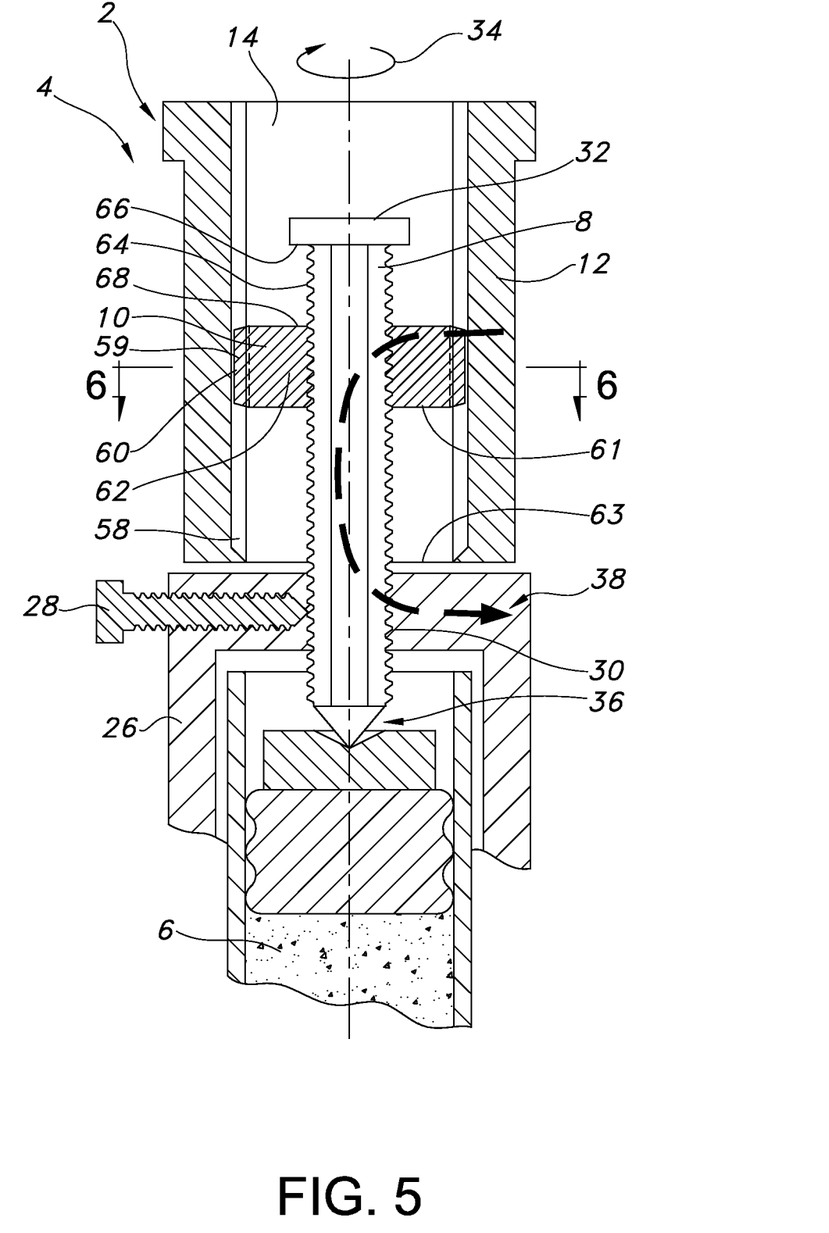
FIG. 5 illustrates a mechanism according to the second general embodiment of the invention.

FIG. 5 discloses the mechanism according to the second general embodiment of the invention. Identical reference numbers refer to identical elements. In FIG. 5 the driver 12 is coupled to a dose setting member (not shown) such that rotation of the dose setting member during dose setting, causes the driver to rotate in the same direction—both when dialling up and down. The inner surface of the driver 12 comprises a groove 58 which is adapted to engage a corresponding radially extending spline 60 of the limiter 10. Accordingly, the driver 12 and the limiter 10 are locked for relative rotational movement, while relative translational movement is possible. Furthermore, the limiter 10 has a threaded inner surface 62 which engages a corresponding threaded outer surface 64 of the piston rod 8. Accordingly, relative rotation between the piston rod and the driver results in relative translational movement between the limiter and each of the piston rod and the driver.

Unlike FIG. 1 the device of FIG. 5 does not comprise first and second sets of teeth. However, it will be appreciated that such sets of teeth could have been provided in the same manner as in FIG. 1. The only difference is that such sets of teeth should have been provided on the surface 66 and on the other, upper side of the limiter as the limiter moves in the direction of the proximal end 32 when a dose is set, as will be described in the following.

In the initial state i.e. when the pen is delivered to the user, the limiter is located in a reference position wherein a surface 61 of the limiter engages a surface 63 of the housing 26. In some embodiments the surfaces 61,63 are spaced apart when the limiter is positioned in the reference position.

In order to set a dose the user locks the piston rod for rotation by means of the locking means 28. The dose is then set by rotating the driver as indicated by arrow 34. Due to the relative rotational movement between the piston rod 8 and the driver 12 the limiter moves towards a proximal end 32 of the piston rod.

When the desired dose has been set, the driver, the limiter and the piston rod are locked rotationally in relation to each other such that, when a dose is ejected, they all rotate together. Due to the threaded engagement 30 between the housing and the piston rod 8, the rotation of the piston rod causes the piston rod to move in the distal direction. Due to the grove-spline connection 59 between the driver and the limiter, the translational movement of the piston rod is not transmitted to the driver. However, due to the threaded connection between the piston rod and the limiter, the limiter will move with the piston rod and arrive at the reference position, i.e. the position it had prior to setting the dose. Accordingly, as described in the aforementioned, the invention according to the second general embodiment does not have the accumulative effect which is seen in connection with the invention according to first general embodiment (FIG. 1-4). On the contrary the limiter returns to the reference position during ejecting of the set dose. This may be used to provide a safety mechanism adapted to prevent ejection of a dose exceeding the set dose, this is described in further detail in connection with FIG. 8.

At a point the piston rod arrives in the stopping position wherein a first stopping thread 66 of the thread 64 of the piston rod engages a second stopping thread 68 of the limiter. The result is that a set dose may not be increased and any torque applied to the driver is transferred to the limiter due to the grove-spline-connection and further to the piston rod due to the stopping thread and finally from the piston rod to the housing—this is indicated by arrow 38. As the piston rod is locked in relation to the housing by means of the locking means 28, further rotation of the driver is not possible.

Figure 6:
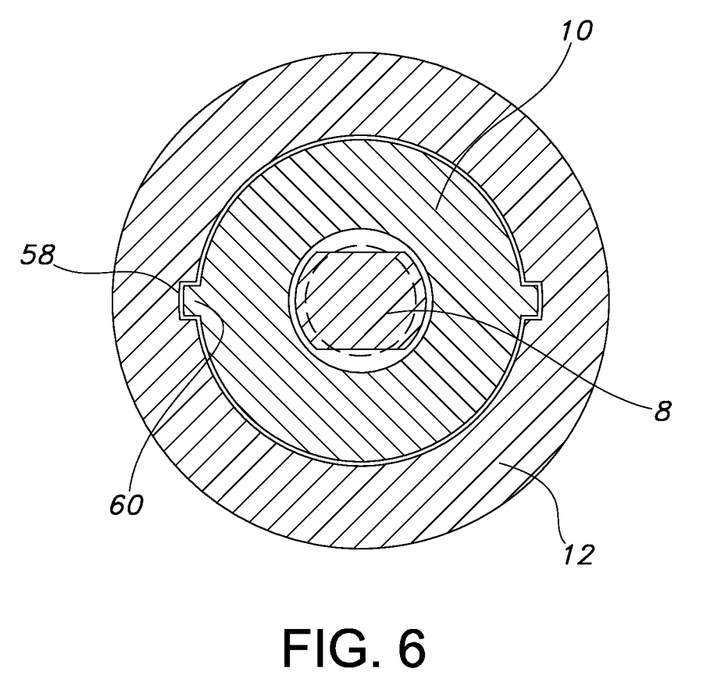
FIG. 6 illustrates a cross-section through the piston rod, the limiter and the driver of FIG. 2.

FIG. 6 discloses a cross-section through the piston rod 8, the limiter 10 and the driver 12. The limiter 10 is locked for rotational movement relative to the driver 12 due to engagement between the groove 58 and the radially extending spline 60 of the limiter 10.

Figure 7:
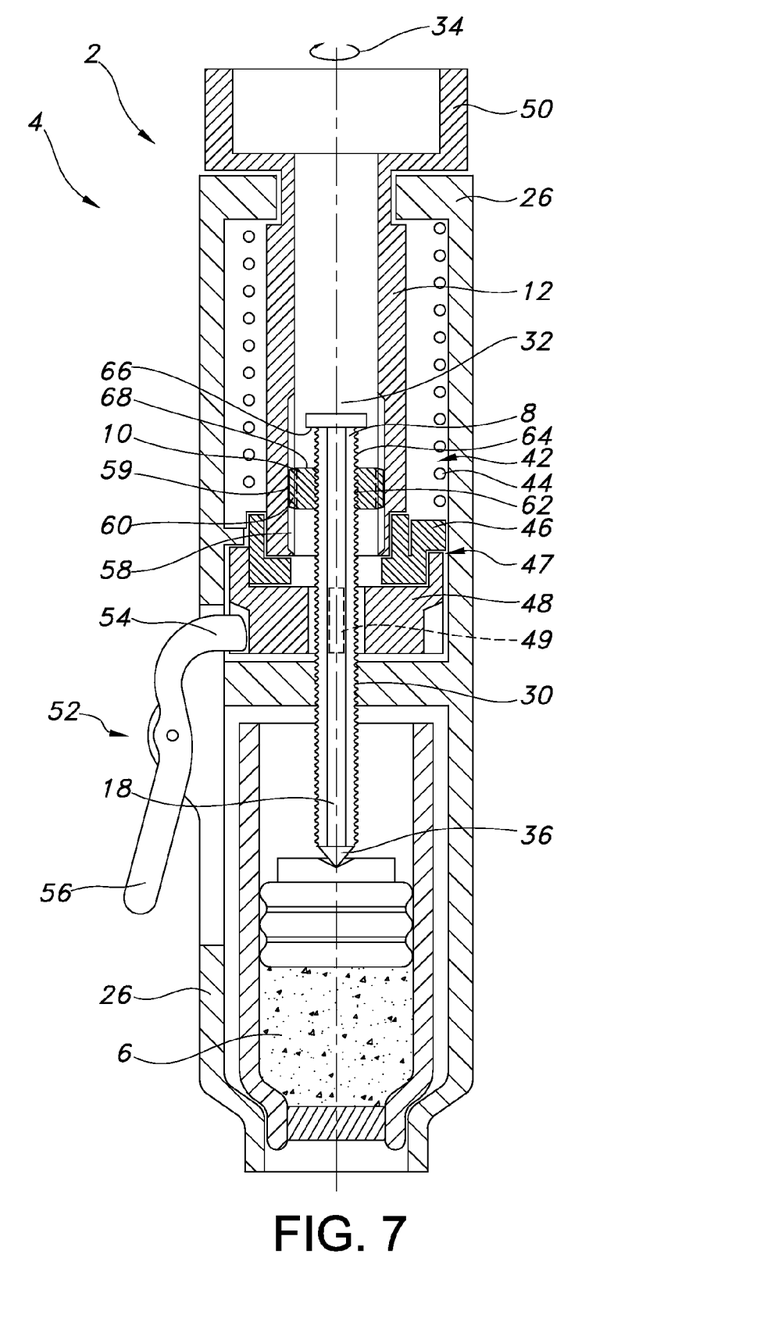
FIG. 7 illustrates a syringe device with injection assisting means and a mechanism according to the second general embodiment of the invention.

FIG. 7 discloses a syringe device 2 comprising the mechanism 4 described in relation to FIG. 5. However, the syringe device of FIG. 6 further comprises an injection assisting mechanism 42 comprising a spring 44 interconnecting the housing 26 and a first part 46 of a ratchet mechanism 47, which further comprises a second part 48. When the dose setting member 50 is rotated, the rotation is transferred to the driver 12 and the first part 46 of the ratchet mechanism. During the rotation of the dose setting member 50, the pre-strained spring 44 is strained even more whereby further potential energy is stored. The stored energy may be released by disengaging the pawl 52 which during dose setting engages the second part 48 of the ratchet mechanism. The pawl 52 is pivotally connected to the housing and comprises an engaging part 54 and a button part 56. When the pawl is disengaged the strained spring 44 causes the first part 46 to rotate. Due to the engagement between the first part 46 and the second part 48, and due to the grove-tongue connection 49 between the first part 46 and the piston rod 8, the rotation of the first part 46 causes the piston rod to rotate. As described under FIG. 1 the rotation of the piston rod causes the piston rod to move forward.

Figure 8:
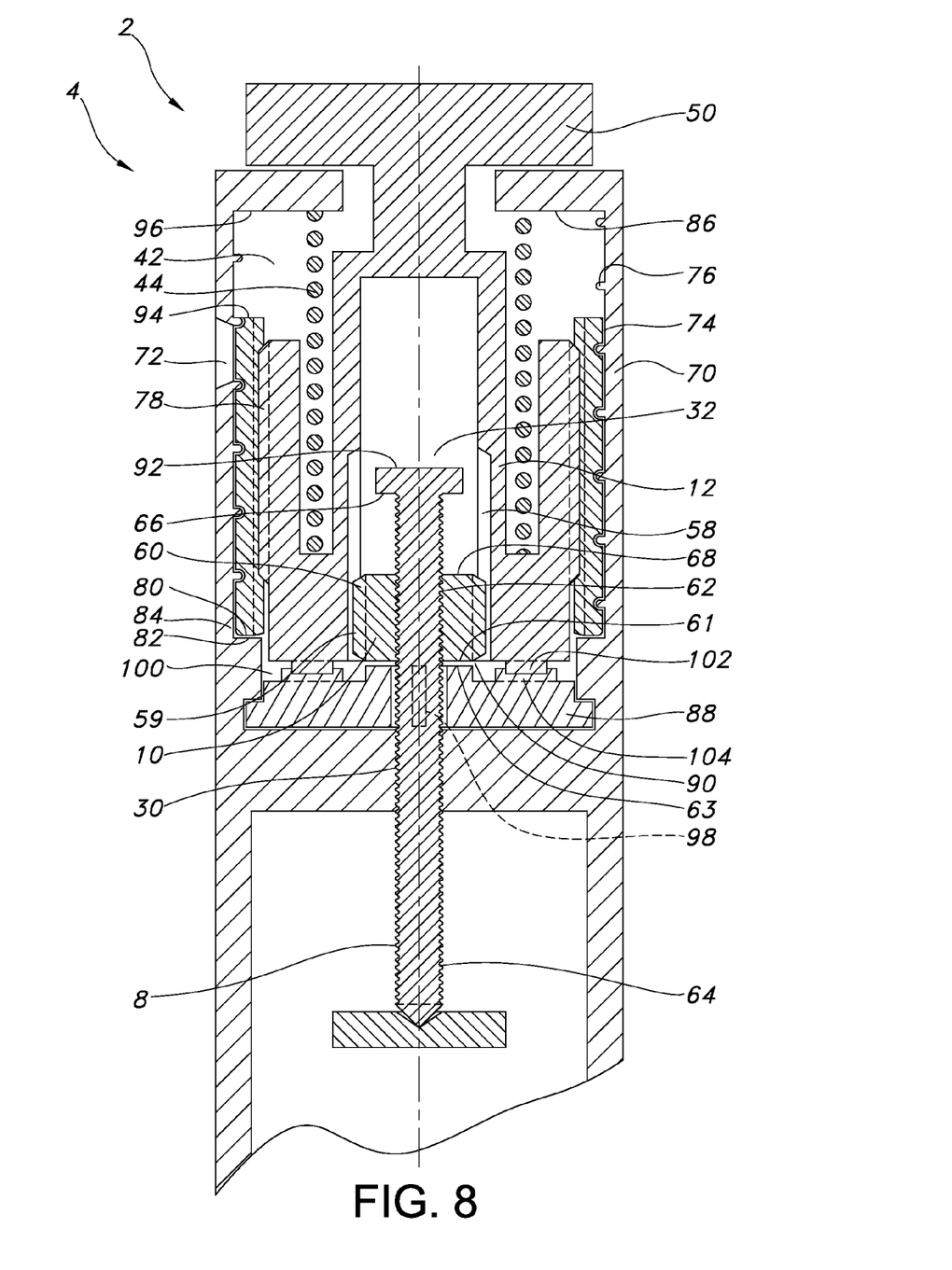
FIG. 8 illustrates a syringe device according to the second general embodiment of the invention wherein the limiter is used both as an end-of-content and as a safety mechanism.

In the embodiment disclosed in FIG. 8 the syringe device comprises means for preventing ejection of a dose exceeding the set dose. Said means comprises a dose limiting mechanism and a safety mechanism as will be described in detail below. An advantage of the two redundant mechanisms is that if one fails the other may still prevent ejection of a dose exceeding the set dose. The embodiment of FIG. 8 further comprises an end-of-content mechanism.

FIG. 8 discloses a syringe device 2 comprising a housing 4 and a piston rod 8. The syringe device 2 further comprises a dose setting member 50 and a driver 12, which in the figure are combined into one single unit. The syringe device further comprises a scale drum 70 for indicating a set dose through a window 72. The scale drum 70 has a threaded outer surface 74 adapted to engage a corresponding threaded inner surface 76 of the housing. The scale drum 70 is rotationally retained relative to the driver 12 through a grove-tongue engagement 78. The drum scale 70 comprises a first stopping surface 80 adapted to engage a second stopping surface 82 of the housing. The first stopping surface 80 and the second stopping surface 82 constitutes the dose limiting mechanism 84. The first stopping surface 80 is moved away from the second stopping surface 82 during dose setting and towards each other during dose ejecting. When the two surfaces abut each other, the device is prevented from ejecting the medicament. Thus, a dose larger than the set dose cannot be expelled as the first and second stopping surfaces abut when the set dose has been expelled The syringe device comprises an ejection assisting system 42 in the form of a pre-strained torsional spring 44 extending between a proximal part 86 of the housing and the driver 12. Accordingly, when the dose setting member 50 is rotated to set a dose, the spring 44 is strained even further.

The piston rod 8 comprises a threaded outer surface 64 adapted to engage a corresponding threaded inner surface 30 of the housing and accordingly rotation of the piston rod relative to the housing causes the piston rod to move translationally in relation to the housing. The threaded outer surface 64 of the piston rod also engages a threaded inner surface 62 of a limiter 10, which in FIG. 8 is positioned in a stopping position wherein a bottom surface 61 of the limiter engages an upper surface 63 of a piston rod guide 88. The bottom surface 61 and the upper surface 63 constitute the safety mechanism 90. An air gap may be provided between the bottom surface 61 and the upper surface 63 when the limiter is in said stopping position, which allows the limiter and the piston rod to rotate and angel corresponding to a non-lethal dose e.g. 3 IU of insulin, if the dose limiting mechanism 84 fails.

Moreover, an upper end-of-contend surface 68 of the limiter 10 is adapted to engage a lower end-of-contend surface 66 of a T-shaped end part 92 of the piston rod. The end-of-contend surfaces are adapted to engage when the set dose correspond to the amount of a medicament remaining in a reservoir (not shown) of the device. Accordingly, the engagement of the end-of-contend surfaces prevents setting of a dose exceeding the amount of a medicament remaining in the reservoir. It will be appreciated that the distance between the end-of-contend surfaces thus corresponds to the amount of the medicament remaining in the reservoir.

Moreover, an upper surface 94 of the drum 70 may be adapted to engage a lower surface 96 of the housing, when the maximum dose is set. The maximum dose is the largest dose which may be set for each ejection (provided that the syringe device comprises the required amount of medicament). The maximum dose does not correspond to the end-of-content dose which relates the remaining amount of a medicament in the device. Accordingly, as long as the remaining amount of medicament in the device is larger than the maximum dose, the end-of-content surfaces will not abut each other during dose setting, whereas when the remaining amount of medicament in the device is lower than the maximum dose, the maximum dose surfaces may abut each other during dose setting, as the end-of-content surfaces prevents further rotation.

The limiter 10 and the driver 12 are locked for relative rotation by means of grove-tongue engagement 59. Thus, when the piston rod is locked for rotation relative to the housing, a relative rotation between the driver 12 and the piston rod 8 causes the limiter to move away from the stopping position and towards the t-shaped end part 92 (i.e. upwards in the figure). The piston rod is locked for rotation relative to the housing when the piston rod guide 88 is locked for rotation relative to the housing (not shown), as the piston rod guide 88 and the piston rod are locked for relative rotation due to the grove-tongue engagement 98.

The driver 12 and the piston rod guide 88 are interconnected by a two-way ratchet mechanism 100 comprising at least one first retaining member 102 defined by the driver 12 and at least one second retaining member 104 defined by the piston rod guide 88. The two-way ratchet mechanism is adapted to allow relative rotational movement between the driver 12 and the piston rod guide 88 during dose setting and to ensure that rotational movement of the driver during dose ejection is transferred to the piston rod guide 88.

The use of the device is as follows. Initially the piston rod guide is locked for rotation relative to the housing. Then the dose setting member is rotated which causes the driver and the drum scale to rotate and the pre-strained spring to be strained even further. At the same time, the limiter moves towards the T-shaped end part. If the user tries to set a dose exceeding the amount of medicament in the device, the limiter abuts the T-shaped end part whereby an even larger dose cannot be set. The dose is ejected by removing the rotational lock between the piston rod guide and the housing, whereby the strained spring forces the driver to rotate. The rotating driver forces the piston rod guide to rotate which again forces the piston rod to rotate. Due to the grove-tongue engagement 44 and the threaded interconnection between the piston rod and the housing, the rotating piston rod is forced to move forward and thus the medicament is expelled from the device.

The invention claimed is:

1. A mechanism for preventing setting of a dose which exceeds the amount of a medicament in a reservoir in an injection device, wherein a dose is set by rotating a dose setting member of a dose setting mechanism, the mechanism comprising:
   a piston rod having a threaded outer surface, wherein the piston rod rotates and translates axially forward during expelling of medication from the reservoir;
   a limiter that prevents the setting of a dose which exceeds the amount of medication in a reservoir in the device, the limiter defining a passage for the piston rod;
   a driver defining a passage for the limiter, the driver being coupled to the dose setting member such that rotation of the dose setting member during dose setting causes the driver to rotate; and
   wherein the limiter is coupled to the driver and the piston rod such that relative rotation between the driver and the piston rod during dose setting causes the limiter to move towards a stopping position.

2. A mechanism according to claim 1, further comprising a housing defining a passage for the piston rod, the passage having a threaded inner surface for engagement with the threaded outer surface of the piston rod, the housing being arranged with respect to the piston rod such that rotation of the piston rod in relation to the housing causes the piston rod to be displaced relative to the housing in a longitudinal direction.

3. A mechanism according to claim 1, further comprising a locking means for locking the piston rod against rotation in at least one direction relative to the housing.

4. A mechanism according to claim 1, wherein:
   the limiter has a threaded outer surface and is rotationally retained in relation to the piston rod; and
   the passage of the driver has a threaded inner surface for engagement with the threaded outer surface of the limiter.

5. A mechanism according to claim 1, wherein the limiter comprises a first engaging surface adapted to engage a corresponding second engaging surface of the driver.

6. A mechanism according to claim 1, wherein the limiter comprises a plurality of teeth adapted to engage corresponding teeth of the housing and/or the driver when the limiter is in the stopping position.

7. A mechanism according to claim 1, wherein:
   the passage of the limiter has a threaded inner surface for engagement with the threaded outer surface of the piston rod; and
   the driver is rotationally retained in relation to the limiter.

8. A mechanism according to claim 1, wherein the limiter comprises a first engaging surface adapted to engage a corresponding second engaging surface of the piston rod.

9. A mechanism according to claim 5, wherein the threaded outer surface of the piston rod comprises the first engaging surface and the threaded inner surface of the driver comprises the second engaging surface.

10. A mechanism according to claim 1, further comprising a ratchet mechanism interconnecting the driver and the housing.

11. A mechanism according to claim 10, wherein the ratchet mechanism comprises a first and a second part, the first part being coupled to the driver and the second part being adapted to be locked for rotation relative to the housing by means of the locking means.

12. A mechanism according to claim 10, further comprising an ejection assisting system for providing an ejection force for assisting an operator during ejection.

13. A syringe device according to claim 12, wherein the ejection assisting system comprises a spring which is strained when the dose setting member is rotated during dose setting.

* * * * *